United States Patent
San Roman Macia et al.

(10) Patent No.: US 11,319,265 B2
(45) Date of Patent: May 3, 2022

(54) SEPARATION OF ETHANE OXIDATIVE DEHYDROGENATION EFFLUENT

(71) Applicant: SHELL OIL COMPANY, Houston, TX (US)

(72) Inventors: Maria San Roman Macia, Ras Laffan (QA); Pejman Pajand, Amsterdam (NL); Ivana Daniela Esposito Cassibba, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 17/289,452

(22) PCT Filed: Oct. 31, 2019

(86) PCT No.: PCT/EP2019/079792
§ 371 (c)(1),
(2) Date: Apr. 28, 2021

(87) PCT Pub. No.: WO2020/074748
PCT Pub. Date: Apr. 16, 2020

(65) Prior Publication Data
US 2021/0387931 A1 Dec. 16, 2021

(30) Foreign Application Priority Data
Nov. 2, 2018 (EP) .................................. 18204144

(51) Int. Cl.
*C07C 7/00* (2006.01)
*B01D 3/14* (2006.01)
(Continued)

(52) U.S. Cl.
CPC .............. *C07C 7/005* (2013.01); *B01D 3/143* (2013.01); *C07C 5/48* (2013.01); *C07C 7/04* (2013.01)

(58) Field of Classification Search
CPC .. C07C 7/005; C07C 5/48; C07C 7/04; B01D 3/143
See application file for complete search history.

(56) References Cited

U.S. PATENT DOCUMENTS

| 3,829,521 A | 8/1974 | Green |
| 4,250,346 A | 2/1981 | Young et al. |
(Continued)

FOREIGN PATENT DOCUMENTS

| CA | 1262556 | 10/1989 |
| CN | 1208669 A | 2/1999 |
(Continued)

OTHER PUBLICATIONS

Yang et al., "Review on the Methods of Separation and Recovery of Acetic Acid From Aqueous Solution", Applied Environmental Protection of Chemical Industry, vol. 15, Issue No. 2, Apr. 30, 1995, 6 pages (English Abstract Only).
(Continued)

*Primary Examiner* — Ali Z Fadhel
(74) *Attorney, Agent, or Firm* — Shell USA, Inc.

(57) ABSTRACT

The invention relates to a process for the production of ethylene by oxidative dehydrogenation of ethane, comprising: a) subjecting a stream comprising ethane to oxidative dehydrogenation conditions, resulting in a stream comprising ethylene, unconverted ethane and light components; b) subjecting ethylene, unconverted ethane and light components from the stream resulting from step a) to distillation, resulting in a stream comprising ethylene and light components and a stream comprising unconverted ethane; c) optionally recycling unconverted ethane from the stream comprising unconverted ethane resulting from step b) to step a); and d) subjecting ethylene and light components from the stream comprising ethylene and light components resulting from step b) to distillation at a top column pressure which is
(Continued)

higher than the top column pressure in step b), resulting in a stream comprising light components and a stream comprising ethylene.

8 Claims, 2 Drawing Sheets

(51) Int. Cl.
*C07C 7/04* (2006.01)
*C07C 5/48* (2006.01)

(56) References Cited

U.S. PATENT DOCUMENTS

| | | | |
|---|---|---|---|
| 4,299,800 A | 11/1981 | Nishikawa et al. | |
| 4,430,102 A * | 2/1984 | Tedder | C07C 7/04 62/628 |
| 4,524,236 A | 6/1985 | McCain | |
| 4,596,787 A | 6/1986 | Manyik et al. | |
| 4,720,293 A | 1/1988 | Rowles et al. | |
| 4,920,088 A | 4/1990 | Kolts | |
| 4,956,330 A | 9/1990 | Elliott et al. | |
| 5,157,204 A | 10/1992 | Brown et al. | |
| 5,258,340 A | 11/1993 | Augustine et al. | |
| 5,430,181 A | 7/1995 | Arpentinier et al. | |
| 5,446,232 A | 8/1995 | Chen et al. | |
| 5,534,650 A | 7/1996 | Ushikubo et al. | |
| 6,518,476 B1 | 2/2003 | Culp et al. | |
| 6,747,066 B2 | 6/2004 | Wang et al. | |
| 6,852,877 B1 | 2/2005 | Zeyss et al. | |
| 7,091,377 B2 | 8/2006 | Borgmeier et al. | |
| 7,390,918 B2 | 6/2008 | Clarke et al. | |
| 7,553,888 B2 | 6/2009 | Greenwood et al. | |
| 8,242,048 B2 | 8/2012 | Rosen | |
| 8,273,680 B2 | 9/2012 | Raichle et al. | |
| 8,524,927 B2 | 9/2013 | Mazanec et al. | |
| 9,187,647 B2 | 11/2015 | Greenwood et al. | |
| 9,249,317 B2 | 2/2016 | Greenwood et al. | |
| 9,738,585 B2 | 8/2017 | Karime | |
| 10,329,222 B2 | 6/2019 | Bos et al. | |
| 2004/0147393 A1 | 7/2004 | Hibst et al. | |
| 2004/0176656 A1 | 9/2004 | Allison et al. | |
| 2005/0085678 A1 | 4/2005 | Lopez Nieto et al. | |
| 2005/0107650 A1 | 5/2005 | Sumner | |
| 2007/0112236 A1 | 5/2007 | Bridges et al. | |
| 2008/0221374 A1 | 9/2008 | Crone et al. | |
| 2009/0281345 A1 | 11/2009 | Matusz | |
| 2009/0312591 A1 | 12/2009 | Schubert et al. | |
| 2010/0069659 A1 | 3/2010 | Raichle et al. | |
| 2010/0069660 A1 | 3/2010 | Raichle et al. | |
| 2010/0222623 A1 | 9/2010 | Ryan | |
| 2010/0256432 A1 | 10/2010 | Arnold et al. | |
| 2011/0212384 A1 | 9/2011 | Luo et al. | |
| 2012/0190900 A1 | 7/2012 | Neston et al. | |
| 2014/0114109 A1 | 4/2014 | Sanchez Valente et al. | |
| 2014/0249339 A1 | 9/2014 | Simanzhenkov et al. | |
| 2015/0133686 A1 | 5/2015 | Macht et al. | |
| 2015/0202602 A1 | 7/2015 | Shu et al. | |
| 2016/0237005 A1 | 8/2016 | Kumar et al. | |
| 2016/0326070 A1 | 11/2016 | Winkler et al. | |
| 2017/0226030 A1 | 8/2017 | Li et al. | |

FOREIGN PATENT DOCUMENTS

| | | |
|---|---|---|
| CN | 1269258 A | 10/2000 |
| CN | 1269341 A | 10/2000 |
| CN | 101041135 A | 9/2007 |
| CN | 101045214 A | 10/2007 |
| CN | 103086821 A | 5/2013 |
| CN | 103121891 A | 5/2013 |
| CN | 103965002 A | 8/2014 |
| CN | 104114278 A | 10/2014 |
| CN | 103551148 B | 8/2015 |
| DE | 102005000798 A1 | 7/2006 |
| EP | 0421169 A1 | 4/1991 |
| EP | 0261264 B1 | 8/1991 |
| EP | 2606963 A1 | 6/2013 |
| GB | 1314613 A | 4/1973 |
| JP | 2014224070 A | 12/2014 |
| WO | 0224614 A1 | 3/2002 |
| WO | 2004035474 A1 | 4/2004 |
| WO | 2010053459 A1 | 5/2010 |
| WO | 2010096909 A1 | 9/2010 |
| WO | 2012101069 A1 | 8/2012 |
| WO | 2012101092 A1 | 8/2012 |
| WO | 2012118888 A2 | 9/2012 |
| WO | 2013108045 A2 | 7/2013 |
| WO | 2013164418 A1 | 11/2013 |
| WO | 2015057753 A1 | 4/2015 |
| WO | 2015082598 A1 | 6/2015 |

OTHER PUBLICATIONS

Ya et al., "Structure and Catalytic Properties Deposited Oxide-molybdenum, Oxide-vanadium and Chromium Oxide Dehydrogenation Catalysts Hydrocarbons", Applied Bulletin of Kuzbass University, 2007, pp. 73-93.
International Search Report and Written Opinion received for PCT Patent Application No. PCT/EP2019/079792, dated Jan. 27, 2020, 07 pages.
International Search Report and Written Opinion received for PCT Patent Application No. PCT/EP2018/054084 dated Apr. 26, 2018, 09 pages.
Zimmermann et al., "Ethylene", Ullmann's Encyclopedia of Industrial Chemistry, Apr. 15, 2009, pp. 1-66. XP055007506.
International Search Report and Written Opinion received for PCT Patent Application No. PCT/EP2017/069266, dated Sep. 28, 2017, 12 pages.
Gao et al., "A Molten Carbonate Shell Modified Perovskite Redox Catalyst for Anaerobic Oxidative Dehydrogenation of Ethane", Science Advances, vol. 6, Apr. 24, 2020, 11 pages.
Phase-pure Mo—V—Te—Nb—O M1 Catalysts for Propane Oxidation, 1 page.
Pyrz et al., Supporting information, 2 pages.
Pilar et al., "High Ethylene Production through Oxidative Dehydrogenation of Ethane Membrane Reactors Based on Fast Oxygen-Ion Conductors", ChemCatChem, vol. 3, Issue No. 9, pp. 1503-1508.
International Search Report and Written Opinion received for PCT Patent Application No. PCT/EP2016/071948, dated Nov. 21, 2016, 8 pages.
International Search Report and Written Opinion received for PCT Patent Application No. PCT/EP2016/075591, dated Jan. 13, 2017, 12 pages.
Baca et al., "Bulk oxidation state of the different cationic elements in the MoVTe(Sb)NbO catalysts for oxidation or ammoxidation of propane", Applied Catalysis A: General, vol. 279, Issue No. 1-2, Jan. 28, 2005, pp. 67-77.
Pyrz et al., "Atomic-level imaging of Mo—V—O complex oxide phase intergrowth, grain boundaries, and defects using HAADF-STEM", PNAS, Apr. 6, 2010, vol. 107, No. 14, pp. 6152-6157, and Supporting Information, 2 pages.
Novakova et al., "Propane Oxidation on Mo—V—Sb—Nb Mixed-Oxide Catalysts: 1. Kinetic and Mechanistic Studies",Journal of Catalysis, vol. 211, Issue No. 1, Oct. 1, 2002, pp. 226-234.
"Polyox Water—Soluble Resins", DOW, Form No. 326-00001-0302 AMS, 2002, 24 pages.
"Levasil and Bindzil Colloidal Silica Dispersions", for the adhesive industry—uses and benefits, AkzoNobel, 2011, 6 pages.
Bindzil CC in Waterborne Coating Applications Silane Modified Colloidal Silica—Uses and Benefits, AkzoNobel, 2011, 8 pages.
International Search Report and Written opinion received for PCT Application No. PCT/EP2016/075593, dated Jan. 26, 2017, 8 pages.
Zhang et al., "Progress in the Study of Ethane Dehydrogenation", Chemical Industry and Engineering Progress Catalyst, vol. 39, Issue No. 6, Mar. 16, 2020, pp. 2390-2398.

(56) References Cited

OTHER PUBLICATIONS

Valente, "Chemical, Structural, and Morphological Changes of a MoVTeNb Catalyst during Oxidative Dehydrogenation of Ethane", ACS Catalysis, vol. 4, Issue No. 5, 2014, pp. 1292-1301.
Roussel et al., "Oxidation of Ethane to Ethylene and Acetic Acid by Movnbo Catalysts", Catalysis Today, vol. 99, pp. 77-87.
Roussel et al., "Movo-based Catalysts for the Oxidation of Ethane to Ethylene and Acetic Acid: Influence of Niobium and/or Palladium on Physicochemical and Catalytic Properties", Applied Catalysis A General, vol. 308, Jul. 2006, pp. 62-74.
Nguyen et al., "Optimizing the Efficiency of Movtenbo Catalysts for Ethane Oxidative Dehydrogenation to Ethylene", Catalysis Communications, vol. 21, May 2012, pp. 22-26.
Process Economics Program Report 37C, Acetic Acid, Dec. 2001, 174 pages.

\* cited by examiner

SEPARATION OF ETHANE OXIDATIVE DEHYDROGENATION EFFLUENT

CROSS REFERENCE TO RELATED APPLICATIONS

This is a national stage application of International Application No. PCT/EP2019/079792, filed 31 Oct. 2019, which claims benefit of priority to European Patent Application No. 18204144.2, filed 2 Nov. 2018.

FIELD OF THE INVENTION

The present invention relates to a process for the production of ethylene by oxidative dehydrogenation (oxydehydrogenation; ODH) of ethane which comprises steps of separating ethylene, unconverted ethane and light components, such as carbon monoxide and methane, from ethane ODH effluent.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts.

WO2010115108 discloses a process for the oxidative dehydrogenation of ethane to ethylene, comprising: contacting an ethane feed and an oxygen-containing gas in the presence of an oxidative dehydrogenation catalyst in an oxidative dehydrogenation reaction zone under conditions to oxidatively dehydrogenate at least a portion of the ethane to produce a product stream comprising ethylene, carbon oxides, water, and unreacted oxygen and ethane, wherein an oxygen concentration in the product stream is at least 0.1 mol %; contacting the product stream with an oxygen elimination catalyst in an oxygen elimination reaction zone to combust at least a portion of the oxygen; recovering from the oxygen elimination reaction zone an effluent having a reduced oxygen content; separating water from the effluent; separating carbon oxides and any non-condensable gas(es) from the ethylene and the unreacted ethane; and separating the ethylene from the unreacted ethane.

It is desired to separate ethylene from unconverted ethane and from light components, such as carbon monoxide and methane, in a technically advantageous and efficient way. Therefore, it is an object of the present invention to provide a process which comprises steps of separating ethylene, unconverted ethane and light components from ethane ODH effluent as produced in an ethane ODH step, which combination of separation steps is technically advantageous, efficient and affordable. Such technically advantageous process would preferably result in a lower energy demand and/or lower capital expenditure.

SUMMARY OF THE INVENTION

It was found that the above-mentioned object may be achieved in a process wherein in a first distillation step ethylene and light components are separated from unconverted ethane and in a later, second distillation step ethylene is separated from light components, wherein the top column pressure in said first distillation step is lower than the top column pressure in said second distillation step.

Accordingly, the present invention relates to a process for the production of ethylene by oxidative dehydrogenation of ethane, comprising:

a) subjecting a stream comprising ethane to oxidative dehydrogenation conditions, resulting in a stream comprising ethylene, unconverted ethane and light components;

b) subjecting ethylene, unconverted ethane and light components from the stream resulting from step a) to distillation, resulting in a stream comprising ethylene and light components and a stream comprising unconverted ethane;

c) optionally recycling unconverted ethane from the stream comprising unconverted ethane resulting from step b) to step a); and d) subjecting ethylene and light components from the stream comprising ethylene and light components resulting from step b) to distillation at a top column pressure which is higher than the top column pressure in step b), resulting in a stream comprising light components and a stream comprising ethylene.

DETAILED DESCRIPTION OF THE INVENTION

Figure 1:
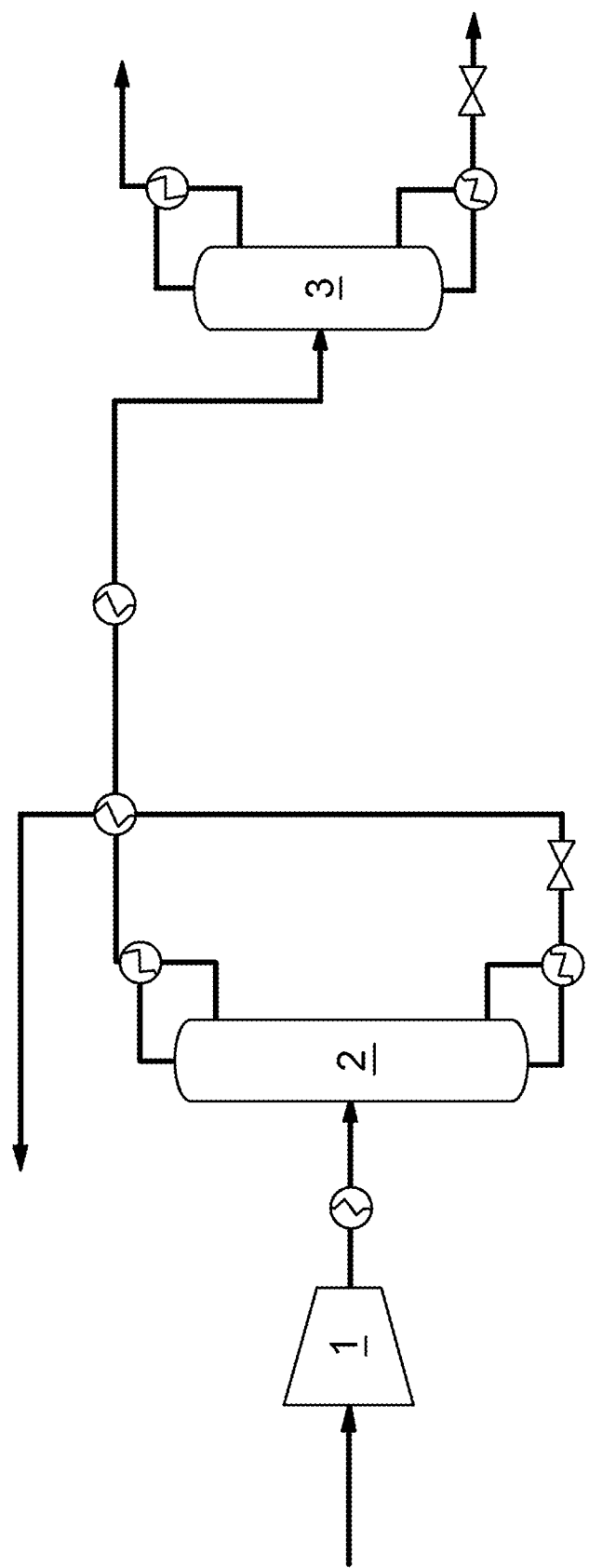
FIG. 1 depicts a process for separating ethylene, ethane and light components which is not in accordance with the present invention.

The process of the present invention comprises steps a), b), c) and d), wherein step c) is optional, as described hereinbelow. Said process may comprise one or more intermediate steps between steps a) and b), between steps b) and c), and between steps c) and d). Further, said process may comprise one or more additional steps preceding step a) and/or following step d).

While the process of the present invention and streams used in said process are described in terms of "comprising", "containing" or "including" one or more various described steps and components, respectively, they can also "consist essentially of" or "consist of" said one or more various described steps and components, respectively.

In the context of the present invention, in a case where a stream or a catalyst comprises two or more components, these components are to be selected in an overall amount not to exceed 100 vol. % or 100 wt. %, respectively.

Further, where upper and lower limits are quoted for a property then a range of values defined by a combination of any of the upper limits with any of the lower limits is also implied.

In the present invention, the light components may comprise one or more components selected from carbon monoxide, methane, nitrogen and carbon dioxide. Said carbon monoxide and carbon dioxide are undesired side-products that may be produced in ethane ODH step a). Further, said methane may be present as a contaminant in the feed of ethane to ethane ODH step a). Still further, said nitrogen may originate from any air used in ODH step a) or may be an impurity in (enriched) oxygen used in ODH step a).

In step b) of the process of the present invention ethylene, unconverted ethane and light components from the stream resulting from ethane oxidative dehydrogenation step (ethane ODH) step a) are subjected to distillation, resulting in a stream comprising ethylene and light components and a stream comprising unconverted ethane. Preferably, in step b) the top column pressure is in the range of from 15 to 25 bara. Further, preferably, in step b) the top column temperature is in the range of from −20 to −45° C. The present invention is characterized in that the top column pressure in said first distillation step b) is lower than the top column pressure in later, second distillation step d).

Thus, surprisingly, in step b) of the present process ethylene, unconverted ethane and light components from the stream resulting from ethane ODH step a) may be compressed to a relatively low pressure before it is subjected to the distillation. This advantageously results in a more energy efficient process. Further, this advantageously results in that the reflux ratio for the distillation column used in said step b) can also be kept relatively low. Furthermore, the purity of ethane and ethylene after separation in the present process is still high. These and other advantages are demonstrated in the Examples below.

In the present invention, step b) is carried out in a distillation column. The number of theoretical stages in the distillation column used in step b) may be of from 80 to 120, preferably 90 to 110. Further, the reflux ratio may be of from 1 to 10, preferably 2 to 8. By said "reflux ratio", reference is made to the molar ratio of the molar flow rate of the "reflux stream", which is that part of the stream that leaves the condenser at the top of the distillation column which is sent back to that column, divided by the molar flow rate of the "distillate", which is that part of the stream that leaves the condenser at the top of the distillation column which is not sent back to that column In optional step c) of the process of the present invention unconverted ethane from the stream comprising unconverted ethane resulting from distillation step b) is recycled to ethane ODH step a).

In step d) of the process of the present invention ethylene and light components from the stream comprising ethylene and light components resulting from distillation step b) are subjected to distillation at a top column pressure which is higher than the top column pressure in distillation step b), resulting in a stream comprising light components and a stream comprising ethylene. In the present invention, it is preferred that the ratio of the top column pressure in step d) to the top column pressure in step b) is at least 1.1, more preferably at least 1.3, more preferably at least 1.5, most preferably at least 1.7. Further, in the present invention, it is preferred that the ratio of the top column pressure in step d) to the top column pressure in step b) is at most 5:1, more preferably at most 4:1, more preferably at most 3:1, most preferably at most 2:1. Preferably, in step d) the top column pressure is in the range of from 20 to 40 bara. Further, preferably in step d) the top column temperature is in the range of from −80 to −110° C. Thus, as described above, the top column pressure in first distillation step b) is lower than the top column pressure in said later, second distillation step d).

In the present invention, step d) is carried out in a distillation column. The number of theoretical stages in the distillation column used in step d) may be of from 30 to 70, preferably 40 to 60. Further, the reflux ratio may be of from 0.1 to 5, preferably 0.5 to 3.

In the present process, the stream comprising ethylene and light components resulting from step b) may be cooled by utilizing the temperature of the stream comprising unconverted ethane resulting from step b), resulting in a cooled stream comprising ethylene and light components. Such cooling can be performed by first expanding (depressurizing) the stream comprising unconverted ethane resulting from step b).

Further, preferably, in the present process, the above-mentioned cooled stream comprising ethylene and light components is separated into a gas stream and a liquid stream, for example in a flash vessel. Said gas stream is compressed and then further cooled, for example by utilizing the temperature of the stream comprising unconverted ethane resulting from step b). Said streams comprising ethylene and light components are then fed to step d) of the present invention. Still further, after cooling one or more of the above-mentioned streams, the stream comprising unconverted ethane resulting from step b) may be recycled to ethane ODH step a).

In step a) of the process of the present invention, a stream comprising ethane is subjected to oxidative dehydrogenation conditions, resulting in a stream comprising ethylene, unconverted ethane and light components.

In step a) of the present process, the stream comprising ethane may be contacted with an oxidizing agent, thereby resulting in oxidative dehydrogenation of the ethane. The oxidizing agent may be any source containing oxygen, such as for example air.

Ranges for the molar ratio of oxygen to ethane which are suitable, are of from 0.01 to 1, more suitably 0.05 to 0.5.

In step a) of the present process, a catalyst may be used which may be a mixed metal oxide catalyst containing molybdenum, vanadium, niobium and optionally tellurium as the metals, which catalyst may have the following formula:

$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is either 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

In step a) of the present process, a catalyst may be used as a pelletized catalyst, for example in the form of a fixed catalyst bed, or as a powdered catalyst, for example in the form of a fluidized catalyst bed.

Examples of oxydehydrogenation processes, including catalysts and other process conditions, are for example disclosed in above-mentioned U.S. Pat. No. 7,091,377, WO2003064035, US20040147393, WO2010096909 and US20100256432, the disclosures of which are herein incorporated by reference.

In step a) of the present process, a catalyst may be used in any amount. The amount of the catalyst in said step a) is not essential. Preferably, a catalytically effective amount of a catalyst is used, that is to say an amount sufficient to promote the ethane oxydehydrogenation reaction. Although a specific quantity of a catalyst is not critical to the invention, preference may be expressed for use of a catalyst in such an amount that the gas hourly space velocity (GHSV) is of from 100 to 50,000 hr$^{-1}$, suitably of from 200 to 20,000 hr$^{-1}$, more suitably of from 300 to 15,000 hr$^{-1}$, most suitably of from 500 to 10,000 hr$^{-1}$.

In step a) of the present process, typical reaction pressures are 0.1-20 bara, and typical reaction temperatures are 100-600° C., suitably 200-500° C.

In general, the product stream resulting from step a) comprises water in addition to the desired product. Water may easily be separated from said product stream, prior to performing step b) of the present process, for example by cooling down the product stream from the reaction temperature to a lower temperature, for example room temperature, so that the water condenses and can then be separated from the product stream.

The invention is further illustrated by the following Examples.

EXAMPLES

Figure 2:
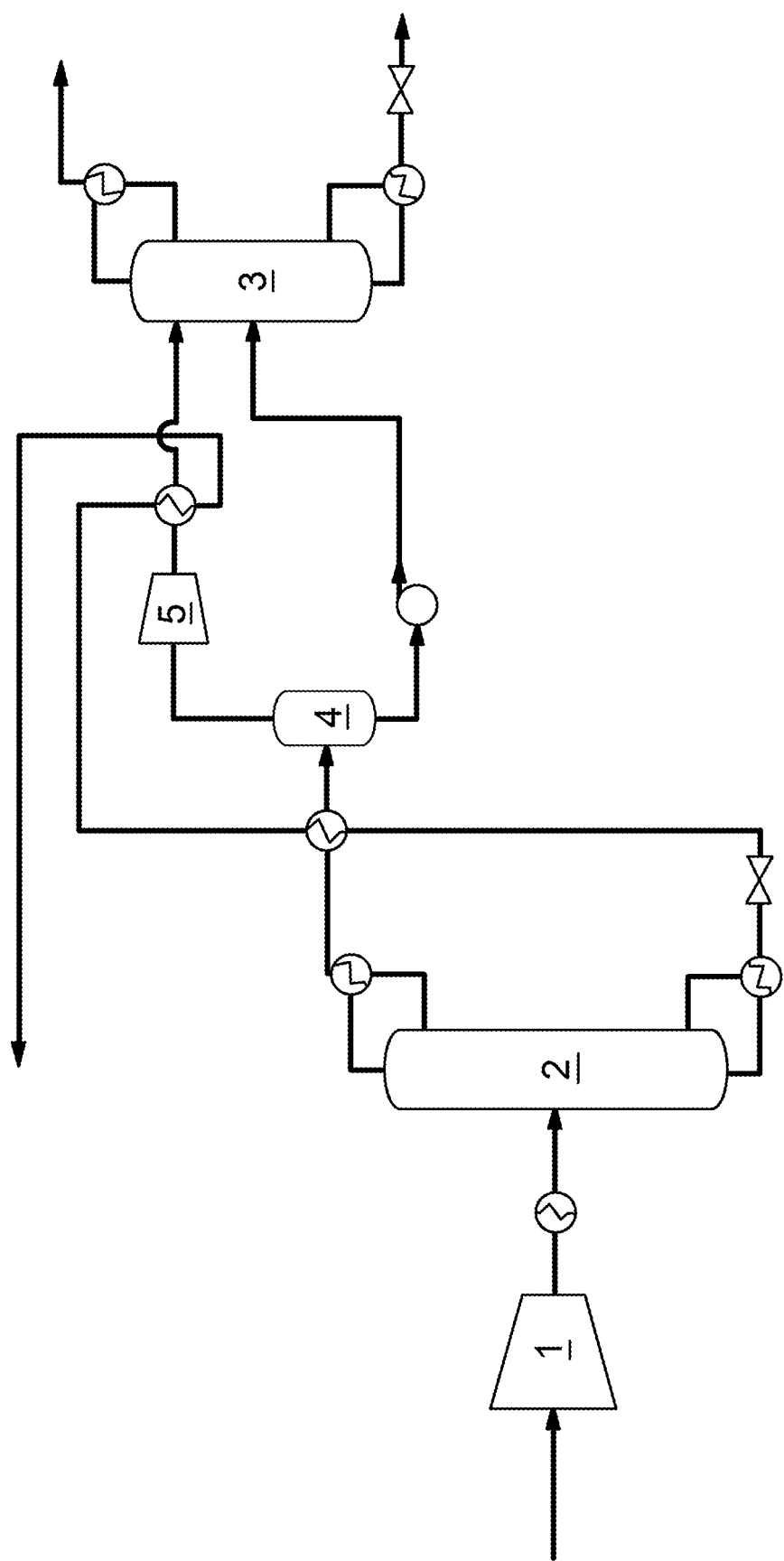
FIG. 2 depicts an embodiment for separating ethylene, ethane and light components which is in accordance with the present invention.

The present invention is illustrated in the Example below and a comparison is made with the Comparison Example below. FIG. 1 schematically shows the setup used in the Comparison Example, whereas FIG. 2 schematically shows the setup used in the Example.

Comparison Example [FIG. 1]

A gas stream comprising 36.6 wt. % of ethylene, 49.6 wt. % of ethane and 13.8 wt. % of light components (carbon monoxide, methane, nitrogen and carbon dioxide), and having a temperature of 38° C. and a pressure of 1.1 bara, is compressed to 36 bara by compressor 1 comprising 4 compression stages and then cooled to a temperature of 2.8° C. in a heat exchanger. Then said stream is fed to distillation column 2 having 120 theoretical stages and distilled (reflux ratio (molar)=10.8), resulting in a top stream (i.e. distillate) comprising ethylene and light components and having a temperature of −17.6° C. and a pressure of 34 bara, and in a bottom stream comprising ethane (ethane purity=99.9 mole %; ethane recovery=99.93%) and having a temperature of 17.3° C. The bottom stream is subjected to a depressurization step resulting in a stream having a temperature of −47.6° C. and a pressure of 6 bara. The cooling duty for the condenser of distillation column 2 is provided by a propane refrigeration cycle (having a temperature of −38° C.).

The above-mentioned top stream comprising ethylene and light components is then cooled to a temperature of −32.7° C. by utilizing the low temperature of the above-mentioned depressurized bottom stream comprising ethane, and is then further cooled to a temperature of −32.9° C. in a heat exchanger. Then said stream is fed to distillation column 3 having 50 theoretical stages and distilled (reflux ratio (molar)=1.7), resulting in a top stream comprising light components and having a temperature of −96° C. and a pressure of 33 bara, and in a bottom stream comprising ethylene (ethylene purity=99.9 mole %; ethylene recovery=99.0%) and having a temperature of −7.9° C. The cooling duty for the condenser of distillation column 3 is provided by an ethylene refrigeration cycle (having a temperature of −98° C.).

Example [FIG. 2]

A gas stream comprising 36.6 wt. % of ethylene, 49.6 wt. % of ethane and 13.8 wt. % of light components (carbon monoxide, methane, nitrogen and carbon dioxide), and having a temperature of 38° C. and a pressure of 1.3 bara, is compressed to 36 bara by compressor 1 comprising 4 compression stages and then cooled to a temperature of 2.8° C. in a heat exchanger. Then said stream is fed to distillation column 2 having 100 theoretical stages and distilled (reflux ratio (molar)=5.3), resulting in a top stream comprising ethylene and light components and having a temperature of −38.5° C. and a pressure of 18.5 bara, and in a bottom stream comprising ethane (ethane purity=99.9 mole %; ethane recovery=99.93%) and having a temperature of −7.5° C. The bottom stream is subjected to a depressurization step resulting in a stream having a temperature of −47.6° C. and a pressure of 6 bara. The cooling duty for the condenser of distillation column 2 is provided by a propane refrigeration cycle (having a temperature of −38° C.).

The above-mentioned top stream comprising ethylene and light components is then cooled to a temperature of −46.6° C. by utilizing the low temperature of the above-mentioned depressurized bottom stream comprising ethane. Then said stream is fed to flash vessel 4 wherein the stream is separated into a gas stream and a liquid stream. The latter gas stream is compressed to 35 bara by compressor 5 comprising 1 compression stage and then further cooled to a temperature of −47.6° C. by utilizing the low temperature of the above-mentioned depressurized bottom stream comprising ethane. Then both said streams are fed to distillation column 3 having 50 theoretical stages and distilled (reflux ratio (molar)=0.9), resulting in a top stream comprising light components and having a temperature of −96° C. and a pressure of 33 bara, and in a bottom stream comprising ethylene (ethylene purity=99.9 mole %; ethylene recovery=99.0%) and having a temperature of −7.9° C. The cooling duty for the condenser of distillation column 3 is provided by an ethylene refrigeration cycle (having a temperature of −98° C.).

In the table below, the compression and refrigeration energy needed to separate (and recover) the components from a stream comprising ethylene, ethane and light components is included for the Comparative Example and the Example. Said energy is expressed as kilowatt hour ("kWh"; 1 kWh=3.6 megajoules) per kilogram (kg) of ethylene.

| Energy [kWh/kg ethylene] | Comparative Example | Example |
| --- | --- | --- |
| Compressor 1 | 0.33 | 0.26 |
| Condenser column 2 | 0.93 | 0.61 |
| Propane compressor | 0.39 | 0.37 |
| Compressor 5 | 0 | 0.01 |
| Condenser column 3 | 0.04 | 0.02 |
| Ethylene compressor | 0.03 | 0.01 |
| TOTAL | 1.72 | 1.28 |

From the table above, it surprisingly appears that the total energy needed to separate (and recover) the components from a stream comprising ethylene, ethane and light components is advantageously lower in the Example, wherein in accordance with the present invention in a first distillation step ethylene and light components are separated from ethane and in a later, second distillation step ethylene is separated from light components, wherein the top column pressure in said first distillation step is lower than the top column pressure in said second distillation step, than the total energy needed in the Comparison Example wherein the top column pressure in said first distillation step is higher than the top column pressure in said second distillation step.

That which is claimed is:

1. A process for the production of ethylene by oxidative dehydrogenation of ethane, comprising:
   a) subjecting a stream comprising ethane to oxidative dehydrogenation conditions, resulting in a stream comprising ethylene, unconverted ethane and light components;
   b) subjecting ethylene, unconverted ethane and light components from the stream resulting from step a) to distillation, resulting in a stream comprising ethylene and light components and a stream comprising unconverted ethane;
   c) optionally recycling unconverted ethane from the stream comprising unconverted ethane resulting from step b) to step a); and
   d) subjecting ethylene and light components from the stream comprising ethylene and light components resulting from step b) to distillation at a top column pressure which is higher than the top column pressure in step b), resulting in a stream comprising light components and a stream comprising ethylene.

2. The process according to claim 1, wherein the ratio of the top column pressure in step d) to the top column pressure in step b) is at least 1.1.

3. The process according to claim 1, wherein the ratio of the top column pressure in step d) to the top column pressure in step b) is at most 5:1.

4. The process according to claim 1, wherein in step b) the top column pressure is in the range of from 15 to 25 bara.

5. The Process according to claim 1, wherein in step d) the top column pressure is in the range of from 20 to 40 bara.

6. The process according to claim 1, wherein in step b) the top column temperature in the range of from −20 to −45° C.

7. The process according to claim 1, wherein in step d) the top column temperature in the range of from −80 to −110° C.

8. The process according to claim 1, wherein the light components comprise one or more components selected from carbon monoxide, methane, nitrogen and carbon dioxide.

* * * * *